United States Patent
Panandikar et al.

(10) Patent No.: US 9,649,319 B2
(45) Date of Patent: May 16, 2017

(54) PROCESS FOR MANUFACTURING STERILE BRINZOLAMIDE OPHTHALMIC SUSPENSION

(71) Applicant: INDOCO REMEDIES LIMITED, Mumbai (IN)

(72) Inventors: Aditi Panandikar, Mumbai (IN); Sundeep Bambolkar, Mumbai (IN); Kavita Inamdar, Mumbai (IN); Sapna Ramesh, Mumbai (IN); Pradnya Bagde, Mumbai (IN)

(73) Assignee: INDOCO REMEDIES LIMITED, Mumbai (IN)

( * ) Notice: Subject to any disclaimer, the term of this patent is extended or adjusted under 35 U.S.C. 154(b) by 0 days.

(21) Appl. No.: 14/433,840

(22) PCT Filed: Oct. 8, 2013

(86) PCT No.: PCT/IN2013/000609
§ 371 (c)(1),
(2) Date: Apr. 6, 2015

(87) PCT Pub. No.: WO2014/057499
PCT Pub. Date: Apr. 17, 2014

(65) Prior Publication Data
US 2015/0250796 A1  Sep. 10, 2015

(30) Foreign Application Priority Data

Oct. 11, 2012  (IN) .................... 2995/MUM/2012

(51) Int. Cl.
| A61K 31/56 | (2006.01) |
| A61K 31/535 | (2006.01) |
| A61K 31/542 | (2006.01) |
| A61K 31/5377 | (2006.01) |
| A61K 9/00 | (2006.01) |
| A61L 2/04 | (2006.01) |

(52) U.S. Cl.
CPC .......... *A61K 31/542* (2013.01); *A61K 9/0048* (2013.01); *A61K 31/5377* (2013.01); *A61K 31/56* (2013.01); *A61L 2/04* (2013.01)

(58) Field of Classification Search
CPC .... A61K 31/56; A61K 31/535; A61K 31/542; A61K 31/5377
See application file for complete search history.

(56) References Cited

U.S. PATENT DOCUMENTS

| 5,378,703 A | 1/1995 | Dean et al. |
| 6,071,904 A | 6/2000 | Ali et al. |
| 2010/0008993 A1 | 1/2010 | Proksch et al. |

FOREIGN PATENT DOCUMENTS

| EP | 23694637 | 12/2011 |
| WO | 98/25620 | 6/1998 |
| WO | 2011/067791 | 12/2010 |

OTHER PUBLICATIONS

"International Search Report for PCT/IN2013/000609 dated Mar. 28, 2014".
Allen, Jr., et al., "Ansel's Pharmaceutical Dosage Forms and Drug Delivery Systems", 2011, Lippincott Williams & Wilkins, 9th Edition, p. 446.

*Primary Examiner* — Zohreh Fay
(74) *Attorney, Agent, or Firm* — Kramer Amado P.C.

(57) ABSTRACT

The present invention relates to a process for manufacturing sterile Brinzolamide Ophthalmic Suspension. Specifically, the present invention relates to a process for manufacturing sterile ophthalmic suspension comprising Brinzolamide sterilized by Dry Heat Sterilization and pharmaceutical suspension obtained by using the said sterilized Brinzolamide. The present invention also relates to a process of manufacturing sterile ophthalmic suspension comprising combination of Brinzolamide sterilized by Dry Heat Sterilization and beta blocker.

12 Claims, 2 Drawing Sheets

PROCESS FOR MANUFACTURING STERILE BRINZOLAMIDE OPHTHALMIC SUSPENSION

TECHNICAL FIELD

The present invention relates to a process for manufacturing sterile Brinzolamide Ophthalmic Suspension. More particularly, the present invention relates to a process for manufacturing sterile ophthalmic suspension comprising Brinzolamide sterilized by Dry Heat Sterilization. The invention further relates to pharmaceutical suspension obtained by using the sterilized Brinzolamide.

BACKGROUND & PRIOR ART

Brinzolamide is a carbonic anhydrase inhibitor, R 4-ethylamino-3,4-dihydro-2-(3-methoxy)propyl-2H-thieno[3,2-e]-1,2-thiazin-6-sulfonamide 1,1 dioxide, first disclosed in U.S. Pat. No. 5,378,703. It is currently formulated in an ophthalmic suspension sold under the trademark of Azopt®. Process to manufacture Brinzolamide Ophthalmic Suspension has also been disclosed in prior art, U.S. Pat. No. 6,071,904. The aforementioned patent describes a process to manufacture Brinzolamide suspension by autoclaving Brinzolamide and surfactant together followed by ball milling. This milled mixture is then added to the rest of the excipients to form a final suspension.

WO2012053011 ('011) discloses process for preparing sterile ophthalmic suspension. The process involves solubilizing Brinzolamide to get a solution which is aseptically filtered to get a filtrate which is further precipitated to get slurry of Brinzolamide. The sterile slurry of Brinzolamide is further ball milled or jet milled along with surfactants and further processed with suitable excipients.

Another approach disclosed in '011 discloses preparing aqueous solution of Brinzolamide, addition of surfactant to said aqueous solution, filtering, precipitating Brinzolamide, followed by ball milling or jet milling; further suspension vehicle is prepared and autoclaved, eventually added to slurry of Brinzolamide and surfactant.

WO2011067791 also describes another process to manufacture a Brinzolamide suspension. The process involves preparation of the slurry of Brinzolamide, followed by preparation of polymer slurry and preparation of a solution of the preservative along with the tonicity agent. The aforementioned preparations are homogenized and autoclaved followed by a sizing process. The sizing process employs a ball mill, colloidal mill or a microfluidiser. An alternately cited process involves autoclaving of Brinzolamide and the surfactant together followed by a microfluidisation process followed by addition of the rest of the excipients in a sterile manner.

Apart from specific processes claimed in prior art which relate to Brinzolamide preparation, general description with regard to preparation of suspensions containing Carbonic Anhydrase Inhibitors (CAI) are also found in prior art. These references describes preparation of sterile, topical, ophthalmic suspensions containing CAI in different ways: by way of final sterilization of a milled suspension, sterile addition of a sterile milled raw material into a sterile vehicle to form a suspension, or by aseptic addition of a sterile raw material to a sterile menstruum followed by ball milling and aseptic addition of the sterile concentrate into a sterile vehicle. These processes are not completely effective as autoclaving causes the CAI to solubilize but lead to formation of large needle like crystals on cooling down of the suspension. This is not an attractive feature especially when used in the area of Ophthalmic. Ophthalmic suspension demands that the particle size should be extremely small in order to avoid irritation on application. Smaller particle size also helps cover larger surface areas and quicker action. The desired particle size recommended is less than 10 micron.

Aseptic ball milling of the final suspension is also not feasible. This is due to unacceptable shear thinning of the polymer which occurs in the final milling step which affects the viscosity of the final suspension. Prior art also states that dry heat sterilization causes melting of the material. Sterilization by ethylene oxide introduces unacceptable degradation products and residues; gamma irradiation produces degradation products which are not acceptable.

Normally, in dry heat sterilization process, the materials are subjected to heated air at a temperature of 160° C. for 2 to 5 hours and at higher temperature of 180° C. for 1 to 3 hours or less. This conventional dry heat sterilization causes melting of the material i.e. active ingredient, specifically Brinzolamide.

The melting point of Brinzolamide is 131° C. Hence dry heat sterilization at conventional temperature causes melting and degradation of Brinzolamide. In order to avoid this problem and to achieve sterility, active ingredient is dry heat sterilized below 131° C.

Surprisingly, the inventors of the present invention have now found that effective sterilization of dry Brinzolamide can be carried out at a significant lower temperature than that considered necessary for the Dry Heat Sterilization without the problems cited in prior art.

OBJECT OF THE INVENTION

Figure 1:
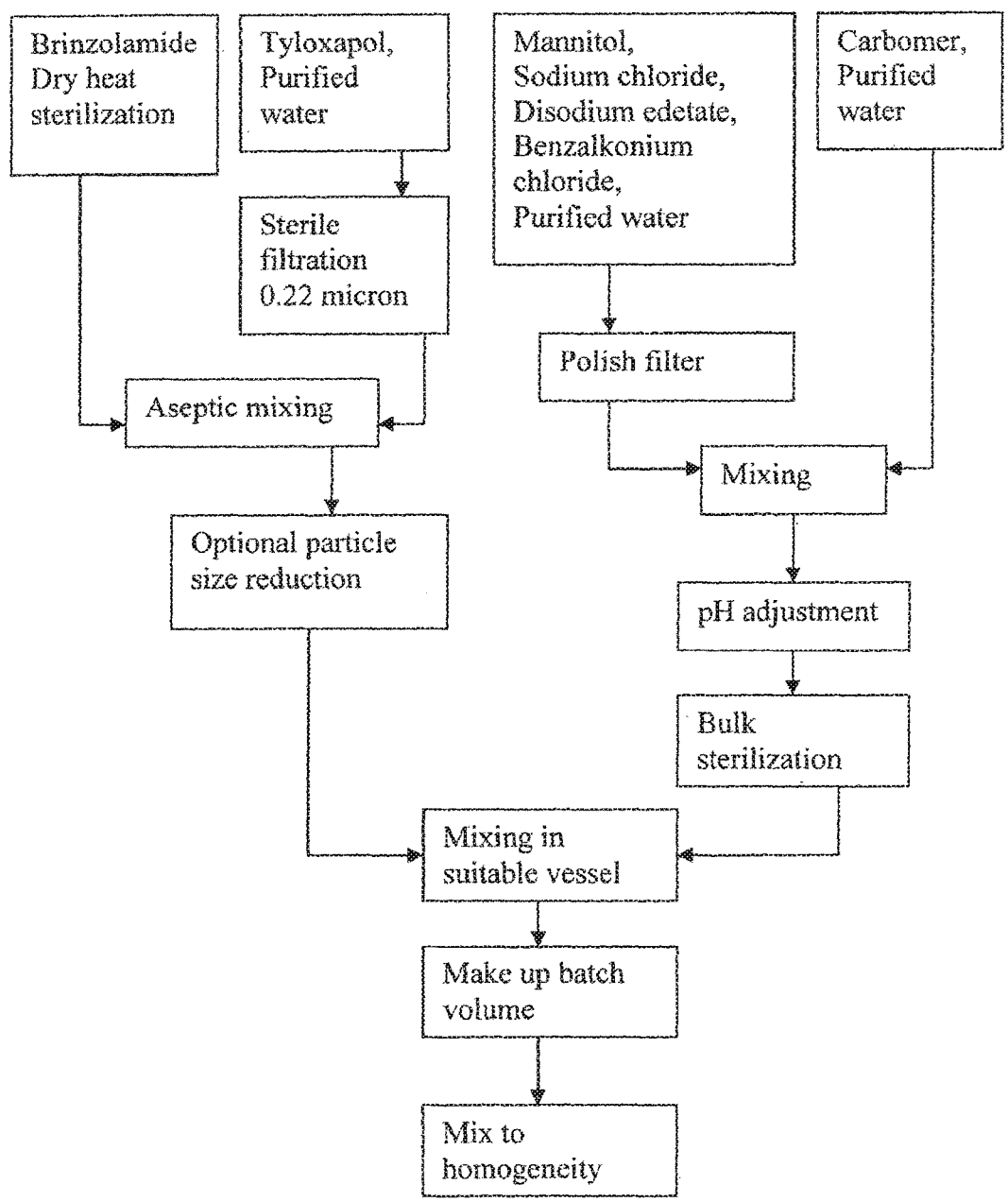
FIG. 1: Flow diagram of a process to manufacture sterile ophthalmic suspension of Brinzolamide.
Figure 2:
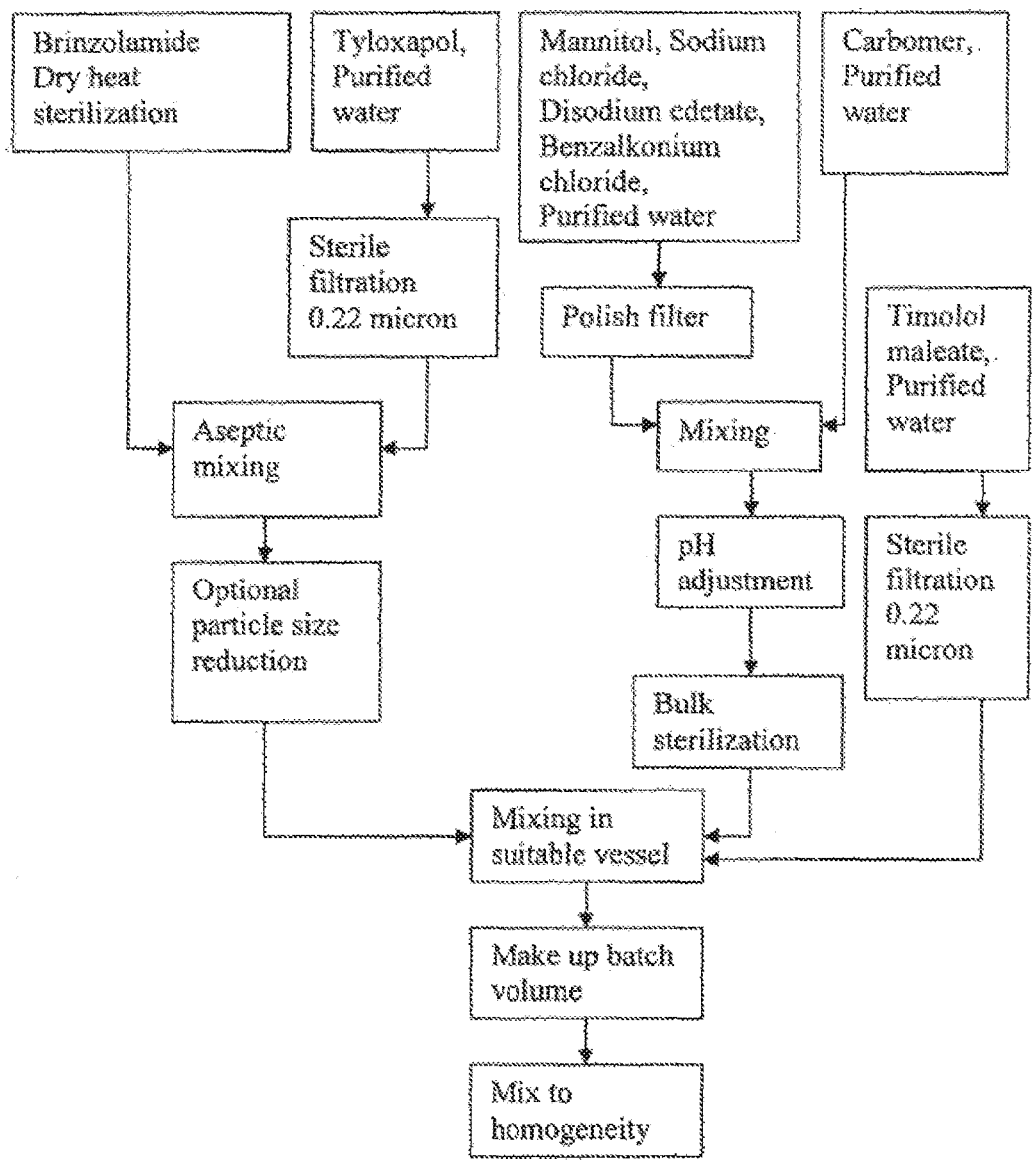
FIG. 2: Flow diagram of a process to manufacture sterile ophthalmic suspension of Brinzolamide and Timolol maleate.

The main object of the present invention is to provide a process for preparing a sterile ophthalmic suspension comprising Brinzolamide sterilized by Dry Heat Sterilization.

Another object of the invention is to provide a sterile ophthalmic suspension of Brinzolamide.

Another object of the present invention is to provide a process for preparing a sterile ophthalmic suspension comprising Brinzolamide sterilized by dry heat sterilization; and beta blocker.

Yet further object of the present invention is to provide a process for preparing a sterile ophthalmic suspension comprising Loteprednol etabonate sterilized by Dry Heat Sterilization.

Yet another object of the invention is to provide a sterile ophthalmic suspension of Brinzolamide for the treatment of elevated intraocular pressure in patients with ocular hypertension or open-angle glaucoma.

Further object of the present invention is to provide a novel, simpler and effective process to prepare sterile ophthalmic suspension of Brinzolamide.

SUMMARY OF THE INVENTION

The present invention relates to a process for preparing a sterile ophthalmic suspension comprising Brinzolamide sterilized by Dry Heat Sterilization.

The present invention provides a process for preparing sterile ophthalmic suspension comprising Brinzolamide, which comprises:
a) sterilization of Brinzolamide by Dry Heat Sterilization;
b) preparation of sterile surfactant solution comprising at least one surfactant;
c) aseptic mixing of Brinzolamide of said 'step a' and surfactant solution of said 'step b' respectively;
d) optionally particle size reduction of the mixture of said 'step c' until homogeneity is obtained;
e) preparation of a solution comprising at least one polymer suitable for ophthalmic use;
f) preparation of a solution comprising at least one tonicity agent and at least one preservative agent;
g) mixing of a solution of said 'step e' and said 'step f' to form a suspension vehicle and adjusting pH;
h) autoclaving of suspension vehicle of said 'step g';
i) aseptically mixing the sterile Brinzolamide of said 'step d' and suspension vehicle of said 'step h' until homogeneity is obtained.

The present invention further provides a process for preparing sterile ophthalmic suspension comprising Brinzolamide and beta blocker.

The present invention also provides a process for preparing sterile ophthalmic suspension comprising Loteprednol etabonate.

DESCRIPTION OF THE INVENTION

The present invention provides a process for preparing a sterile ophthalmic suspension comprising Brinzolamide sterilized by Dry Heat Sterilization.

The process for preparing a sterile ophthalmic suspension comprising Brinzolamide comprises of following steps:
a) sterilization of Brinzolamide by Dry Heat Sterilization;
b) preparation of sterile surfactant solution comprising at least one surfactant;
c) aseptic mixing of Brinzolamide of said 'step a' and surfactant solution of said 'step b' respectively;
d) optionally particle size reduction of the mixture of said 'step c' until homogeneity is obtained;
e) preparation of a solution comprising at least one polymer suitable for ophthalmic use;
f) preparation of a solution comprising at least one tonicity agent and at least one preservative agent;
g) mixing of a solution of said 'step e' and said 'step f' to form a suspension vehicle and adjusting pH;
h) autoclaving of suspension vehicle of said 'step g';
i) aseptically mixing the sterile Brinzolamide of said 'step d' and suspension vehicle of said 'step h' until homogeneity is obtained;

In one embodiment, sterilization of Brinzolamide can be done by dry heating in the form of a powder at a temperature less than 125° C. The sterilization is preferably carried out at a temperature from 80° C.-120° C., more specifically at about 105° C. for 24 hours, preferably for 10 hours. The process is conveniently carried out under atmospheric condition, i.e. air. It can also be carried out under inert gas atmosphere, e.g. argon or nitrogen.

According to another embodiment, sterilization of Brinzolamide can be done by dry heating in the form of finely divided particles having 100% of particles less than 100 microns, preferably less than 50 microns and more preferably less than 30 microns.

In one embodiment, the dry heat sterilization of Brinzolamide is done at a temperature less than 125° C.

According to another embodiment, the Dry Heat Sterilization of Brinzolamide is done at a temperature between 80-120° C. for 5-20 hours.

According to another embodiment, the Dry Heat Sterilization of Brinzolamide is done at a temperature between 100-115° C. for 10-18 hours.

According to preferred embodiment, the Dry Heat Sterilization of Brinzolamide is done at a temperature of 105° C. for 2-10 hours.

In one embodiment, the present invention involves use of high pressure homogenizer for reduction of particle size.

Another embodiment of the present invention involves use of microfluidiser for reduction of particle size.

Another embodiment of the present invention involves use of ball milling for reduction of particle size.

According to another embodiment, the particle size reduction of Brinzolamide or Brinzolamide and surfactant solution can be done by conventional techniques with which those skilled in the art are familiar.

According to another embodiment, the process for preparing sterile ophthalmic suspension comprising Brinzolamide sterilized by Dry Heat Sterilization is without the step of particle size reduction.

According to another embodiment, the present invention involves micronization of Brinzolamide or micronization of Brinzolamide and surfactant solution using conventional techniques with which those skilled in the art are familiar.

The term sterile means a product which meets the criteria of the United States Pharmacopoeia, European Pharmacopeia and which provides a therapeutically acceptable Brinzolamide suspension.

The active pharmaceutical ingredient according to the present invention after Dry Heat Sterilization will essentially contain the same physico-chemical properties, its chemical purity and physical form as the starting material from which it is prepared. The degradation, especially chemical degradation caused by the present sterilization process is negligible. A table of comparison for Related Substance data of Brinzolamide after sterilization by Gamma irradiation and Dry heat sterilization is presented below.

| Impurities | Limit | Gamma sterilized Brinzolamide | Dry Heat Sterilized Brinzolamide |
| --- | --- | --- | --- |
| Related Compound B | NMT 0.3% | 0.4 | 0.01 |
| Related Compound C | NMT 0.3% | 0.06 | 0.06 |
| Related Compound D | NMT 0.3% | 0.01 | 0.01 |
| Any individual impurity | NMT 0.3% | 0.73 | 0.09 |
| Total | NMT 1.0% | 1.98 | 0.43 |

The polymorphic study states that the active pharmaceutical ingredient retains its crystal structure as that of the untreated material.

The present invention relates an aqueous suspension comprising Brinzolamide. Specifically the present invention relates to a method of manufacturing sterile ophthalmic suspension of Brinzolamide or its pharmaceutically acceptable salts, solvates, hydrates, polymorphs, stereoisomers, esters, prodrugs, enantiomers, complexes and their metabolites thereof.

The present process offers a novel, simpler and effective process to manufacture Brinzolamide suspension.

According to another embodiment, the present invention relates to process of preparing ophthalmic suspension for compounds which may be sparingly soluble, slightly soluble, practically insoluble selected from the group but not are not limited to a beta blocker, such as timolol, betaxolol; non steroidal anti inflammatory drugs (NSAID), such as nepefenac, flurbiprofen, diclofenac; steroid such as hydrocortisone, dexamethasone, prednisolone, loteprednol etabonate or medrysone. The above compounds can be used in various combinations.

In accordance with the present invention, sterile ophthalmic suspension comprises of Brinzolamide and one or more of surfactants, tonicity agents, ophthalmically acceptable polymers and preservatives.

Surfactant used in the present invention may be selected from the group comprising polysorbate 80, polysorbate 20, tyloxapol, triton X-100, tween 80, poloxamer, ethoxylated alcohol, propoxylated alcohol and combinations thereof.

Tonicity agent used in the present invention may be selected from a group comprising mannitol, dextrose, glycerin, potassium chloride, sodium chloride, glycerin, boric acid, sorbitol, propylene glycol and combinations thereof.

Polymer used in the present invention may be selected form the group comprising carbomer, povidone, hydroxypropylmethyl cellulose, hydroxypropyl cellulose, hydroxyethyl cellulose, propylene glycol, polyvinyl alcohol and combinations thereof.

Preservative used in the present invention may be selected from the group comprising benzalkonium chloride (BAK), benzyl alcohol, methyl paraben, propyl paraben, thimerosal, chlorobutanol, benzethonium chloride, phenyl ethanol, phenyl propanol, phenyl mercuric acetate, phenyl mercuric nitrate, phenyl mercuric borate, chlorhexidine acetate or gluconate, cetrimide, chlorocresol and combinations thereof.

pH adjusting agent may be selected from the group comprising sodium hydroxide, hydrochloric acid, potassium hydroxide, sodium carbonate, citric acid, phosphoric acid, acetic acid, tartaric acid, sodium hydrogen carbonate and combinations thereof.

According to the present invention, the sterile ophthalmic suspension comprising 0.01 to 1% of Brinzolamide, 0.1 to 10% of surfactant, 0.1 to 10% of tonicity agent, 0.01 to 15% of polymer and 0.05 to 5% of preservative agent.

According to another embodiment, the present invention provides a method for preparing a sterile ophthalmic suspension comprising combination of Brinzolamide and Timolol maleate of following steps:
a) sterilization of Brinzolamide by Dry Heat Sterilization;
b) preparation of sterile surfactant solution comprising at least one surfactant;
c) aseptic mixing of Brinzolamide of said 'step a' and surfactant solution of said 'step b' respectively;
d) optionally particle size reduction of the mixture of said 'step c' until homogeneity is obtained;
e) preparation of a solution comprising at least one polymer suitable for ophthalmic use;
f) preparation of a solution comprising at least one tonicity agent and at least one preservative agent;
g) mixing of a solution of said 'step e' and said 'step f' to form a suspension vehicle and adjusting pH;
h) autoclaving of suspension vehicle of said 'step g';
i) aseptically adding Timolol maleate solution to the mixture of said 'step h';
j) aseptically adding the sterile Brinzolamide of said 'step d' and suspension vehicle of said 'step i' until homogeneity is obtained.

According to another embodiment, the present invention provides a method for preparing a sterile ophthalmic suspension comprising Loteprednol etabonate of following steps:
a) sterilization of Loteprednol etabonate by Dry Heat Sterilization;
b) preparation of sterile surfactant solution comprising at least one surfactant;
c) aseptic mixing of Loteprednol etabonate of said 'step a' and surfactant solution of said 'step b' respectively;
d) optionally particle size reduction of the mixture of said 'step c' until homogeneity is obtained;
e) preparation of a solution comprising at least one ophthalmically acceptable polymer;
f) preparation of a solution comprising at least one tonicity agent and at least one preservative agent;
g) mixing of a solution of said 'step e' and said 'step f' to form a suspension vehicle and adjusting pH;
h) sterilization of suspension vehicle of said 'step g';
i) aseptically adding the sterile Loteprednol etabonate of said 'step d' and suspension vehicle of said 'step h' until homogeneity is obtained;

In one embodiment, the dry heat sterilization of Loteprednol etabonate is done at a temperature below 200° C. for 1-10 hours.

Although the invention has been described with reference to specific embodiments, this description is not meant to be construed in a limiting sense. Various modifications of the disclosed embodiments, as well as alternate embodiments of the invention, will become apparent to person skilled in the art upon reference to the description. It is therefore contemplated that such modifications can be made without departing from the spirit or scope of the present invention as defined.

The invention is further exemplified with following examples and is not intended to limit the scope of the invention.

Example 1

| Sr. No | Ingredients | % w/w |
|---|---|---|
| 1. | Brinzolamide | 1 |
| 2. | Tyloxapol | 0.025 |
| 3. | Carbomer 974P | 0.40 |
| 4. | Disodium EDTA | 0.01 |
| 5. | Benzalkonium chloride | 0.01 |
| 6. | Mannitol | 3.30 |
| 7. | Sodium chloride | 0.25 |
| 8. | Hydrochloric acid or Sodium hydroxide | qs |
| 9. | Purified water | qs |

Manufacturing Process:
Step 1. Brinzolamide API was sterilized by using dry heat sterilization technique at 80-120° C. for 5-20 hours.
Step 2. A solution of tyloxapol was prepared by dissolving tyloxapol in water and this solution was sterilized by filtration through 0.22 micron filter.
Step 3. Aseptically Brinzolamide API was mixed to tyloxapol solution of 'step 2' and this solution of Brinzolamide and tyloxapol was passed through high pressure homogenizer or microfluidiser or ball milling to reduce the particle size.
Step 4. A solution of mannitol, sodium chloride, disodium EDTA and benzalkonium chloride was prepared by dissolving in water as vehicle concentrate and filtered through polish filter.

Step 5. Carbomer slurry was prepared by dispersing carbomer in water and added to the vehicle concentrate of 'step 4' and the pH was adjusted to 7.5±0.2. This slurry of 'step 5' was autoclaved for sterilization.

Step 6. Brinzolamide slurry of 'step 3' and carbopol slurry of 'step 5' was aseptically mixed to get a homogenized suspension.

Example 2

| Sr. No | Ingredients | % w/w |
| --- | --- | --- |
| 1 | Brinzolamide | 1 |
| 2 | Triton X-100 | 0.025 |
| 3 | Carbomer 974P | 0.45 |
| 4 | Disodium EDTA | 0.01 |
| 5 | Benzalkonium chloride | 0.01 |
| 6 | Mannitol | 3.30 |
| 7 | Sodium chloride | 0.25 |
| 8 | Hydrochloric acid or Sodium hydroxide | qs |
| 9 | Purified water | qs |

Manufacturing Process:

Step 1. Brinzolamide API was sterilized by using Dry Heat Sterilization technique at 100-115° C. for 10-18 hours.

Step 2. A solution of triton X-100 was prepared by dissolving triton X-100 in water and this solution was sterilized by filtration through 0.22 micron filter.

Step 3. Aseptically Brinzolamide API was mixed to triton X-100 solution of step 2 and this solution of Brinzolamide and triton X-100 was passed through high pressure homogenizer or microfluidiser or ball milling to reduce the particle size.

Step 4. A solution of mannitol, sodium chloride, disodium EDTA and benzalkonium chloride was prepared by dissolving in water as vehicle concentrate and filtered through polish filter.

Step 5. Carbomer slurry was prepared by dispersing carbomer in water and added to the vehicle concentrate of 'step 4' and the pH was adjusted to 7.5±0.2. This slurry of 'step 5' was autoclaved for sterilization.

Step 6. Brinzolamide slurry of 'step 3' and carbopol slurry of 'step 5' was aseptically mixed to get a homogenized suspension.

Example 3

| Sr. No | Ingredients | % w/w |
| --- | --- | --- |
| 1. | Brinzolamide | 1 |
| 2. | Tyloxapol | 0.025 |
| 3. | Carbomer 974P | 0.425 |
| 4. | Disodium EDTA | 0.01 |
| 5. | Benzalkonium chloride | 0.01 |
| 6. | Mannitol | 3.30 |
| 7. | Sodium chloride | 0.25 |
| 8. | Sodium hydroxide or Hydrochloric acid | qs |
| 9. | Purified water | qs |

Manufacturing Process:

Step 1. Brinzolamide API was sterilized by using Dry Heat Sterilization technique at 105° C. for 2-10 hours.

Step 2. A solution of tyloxapol was prepared by dissolving tyloxapol in water and this solution was sterilized by filtration through 0.22 micron filter.

Step 3. Aseptically Brinzolamide API was mixed to tyloxapol solution of step 2 and this solution of Brinzolamide and tyloxapol was passed through high pressure homogenizer or microfluidiser or ball milling to reduce the particle size.

Step 4. A solution of mannitol, sodium chloride, disodium EDTA and benzalkonium chloride was prepared by dissolving in water as vehicle concentrate and filtered through polish filter.

Step 5. Carbomer slurry was prepared by dispersing carbomer in water and added to the vehicle concentrate of 'step 4' and the pH was adjusted to 7.5±0.2. This slurry of 'step 5' was autoclaved for sterilization.

Step 6. Brinzolamide slurry of 'step 3' and carbopol slurry of 'step 5' was aseptically mixed to get a homogenized suspension.

Example 4

| Sr. No | Ingredients | % w/w |
| --- | --- | --- |
| 1 | Brinzolamide | 1 |
| 2 | Timolol maleate (equivalent to 0.5% Timolol as free base) | 0.025 |
| 3 | Carbomer 974P | 0.45 |
| 4 | Disodium edetate | 0.01 |
| 5 | Benzalkonium chloride | 0.01 |
| 6 | Mannitol | 3.3 |
| 7 | Sodium chloride | 0.10 |
| 8 | Sodium hydroxide or Hydrochloric acid | qs |
| 9 | Purified water | qs |

Manufacturing Process:

Step 1. Brinzolamide API was sterilized by using Dry Heat Sterilization technique at 105° C. for 2-10 hours.

Step 2. A solution of tyloxapol was prepared by dissolving tyloxapol in water and this solution was sterilized by filtration through 0.22 micron filter.

Step 3. Aseptically Brinzolamide API was mixed to tyloxapol solution of 'step 2' and this solution of Brinzolamide and tyloxapol was passed through high pressure homogenizer or microfluidiser or ball milling to reduce the particle size.

Step 4. A solution of mannitol, sodium chloride, disodium EDTA and benzalkonium chloride was prepared by dissolving in water as vehicle concentrate and filtered through polish filter.

Step 5. Carbomer slurry was prepared by dispersing carbomer in water and added to the vehicle concentrate of 'step 4' and the pH was adjusted to 7.5±0.2. This slurry of 'step 5' was autoclaved for sterilization.

Step 6. Aseptically Timolol maleate solution was mixed with slurry of 'step 5'.

Step 7. Brinzolamide slurry of 'step 3' and slurry of 'step 6' was aseptically mixed to get a homogenized suspension.

Example 5

| Sr. No | Ingredients | % w/w |
| --- | --- | --- |
| 1. | Loteprednol etabonate | 1 |
| 2. | Disodium edetate | 0.025 |
| 3. | Benzalkonium chloride | 0.01 |
| 4. | Glycerin | 0.40 |
| 5. | Povidone | 0.01 |

-continued

| Sr. No | Ingredients | % w/w |
|---|---|---|
| 6. | Tyloxapol | 0.01 |
| 7. | Sodium hydroxide or Hydrochloric acid | qs |
| 8. | Purified water | qs |

Manufacturing Process:

Step 1. Loteprednol etabonate API was sterilized by using Dry Heat Sterilization technique below 200° C. for 1-10 hours.

Step 2. A solution of tyloxapol was prepared by dissolving tyloxapol in water and this solution was sterilized by filtration through 0.22 micron filter.

Step 3. Aseptically Loteprednol etabonate API was mixed to tyloxapol solution of 'step 2' and this solution of Loteprednol and tyloxapol was passed through high pressure homogenizer or microfluidiser or ball milling to reduce the particle size.

Step 4. A solution of glycerin, disodium EDTA and benzalkonium chloride was prepared by dissolving in water as vehicle concentrate.

Step 5. Povidone solution was prepared by dissolving povidone in the vehicle concentrate of 'step 4' and the pH was adjusted to 5.5±0.2. This solution of 'step 5' was sterilized by filtration through 0.22 micron filter.

Step 6. Loteprednol etabonate slurry of 'step 3' and povidone solution of 'step 5' was aseptically mixed to get a homogenized suspension.

We claim:

1. A process for preparing a brinzolamide ophthalmic formulation, comprising:
   a) sterilizing brinzolamide by dry heat sterilization at a temperature of between 80° C. and 125° C.;
   b) mixing said brinzolamide with a sterile surfactant solution comprising a surfactant to obtain a slurry;
   c) optionally reducing the particle size of particles within said slurry until homogeneity is obtained;
   d) preparing a suspension vehicle comprising a solution of a polymer suitable for ophthalmic use, a tonicity agent, a preservative agent, and optionally a second drug;
   e) autoclaving said suspension vehicle; and
   f) mixing said slurry and said suspension vehicle to prepare a homogeneous ophthalmic suspension of brinzolamide.

2. The process of claim 1, comprising sterilizing Brinzolamide by Dry Heat Sterilization for between about 5 and about 20 hours.

3. The process of claim 1, comprising sterilizing Brinzolamide by Dry Heat Sterilization at a temperature of between 100° C. and 115° C. for between about 10 and about 18 hours.

4. The process of claim 1, comprising sterilizing Brinzolamide by Dry Heat Sterilization at a temperature of about 105° C. for between about 2 and about 10 hours.

5. The process of claim 1, wherein said second drug is a beta blocker; a non steroidal anti inflammatory drug; a steroid, or a mixture thereof.

6. The process of claim 5, wherein said second drug is a beta blocker.

7. The process of claim 6, wherein said beta blocker is timolol maleate.

8. The process of claim 1, wherein the surfactant is selected from the group consisting of polysorbate 80, polysorbate 20, tyloxapol, triton X-100, tween 80, poloxamer, ethoxylated alcohol, propoxylated alcohol, and mixtures thereof.

9. The process of claim 1, wherein the tonicity agent is selected from the group consisting of mannitol, dextrose, glycerin, potassium chloride, sodium chloride, boric acid, sorbitol, propylene glycol, and mixtures thereof.

10. The process of claim 1, wherein the polymer is selected from the group consisting of carbomer, povidone, hydroxypropylmethyl cellulose, hydroxypropyl cellulose, hydroxyethyl cellulose, propylene glycol, polyvinyl alcohol, and mixtures thereof.

11. The process of claim 1, wherein the preservative agent is selected from the group consisting of benzalkonium chloride (BAK), benzyl alcohol, methyl paraben, propyl paraben, thimerosal, chlorobutanol, benzethonium chloride, phenyl ethanol, phenyl propanol, phenyl mercuric acetate, phenyl mercuric nitrate, phenyl mercuric borate, chlorhexidine acetate, chlorhexidine gluconate, cetrimide, chlorocresol, and mixtures thereof.

12. A process for preparing an ophthalmic formulation comprising a first drug, said first drug being Brinzolamide or a pharmaceutically acceptable salt, solvate, hydrate, polymorph, stereoisomer, ester, prodrug, enantiomer, complex, or metabolite thereof, said process comprising:
   a) sterilizing said first drug by dry heat sterilization at a temperature of between 80° C. and 125° C.;
   b) mixing said first drug with a sterile surfactant solution comprising a surfactant to obtain a slurry;
   c) optionally reducing the particle size of particles within said slurry until homogeneity is obtained;
   d) preparing a suspension vehicle comprising a solution of a polymer suitable for ophthalmic use, a tonicity agent, a preservative agent, and optionally a second drug;
   e) autoclaving said suspension vehicle; and
   f) mixing said slurry and said suspension vehicle to prepare a homogeneous ophthalmic suspension of said first drug.

* * * * *